(12) United States Patent
Takimiya et al.

(10) Patent No.: US 9,209,409 B2
(45) Date of Patent: Dec. 8, 2015

(54) NAPHTHOBISTHIADIAZOLE DERIVATIVE

(71) Applicants: National University of Corporation Hiroshima University, Hiroshima (JP); Sankyo Kasei Co., Ltd., Osaka (JP)

(72) Inventors: Kazuo Takimiya, Hiroshima (JP); Itaru Osaka, Hiroshima (JP); Kazuaki Kawashima, Hiroshima (JP)

(73) Assignees: National University of Corporation Hiroshima University, Hiroshima (JP); Sankyo Kasei Co., Ltd., Osaka (JP)

( * ) Notice: Subject to any disclaimer, the term of this patent is extended or adjusted under 35 U.S.C. 154(b) by 0 days.

(21) Appl. No.: 14/395,774

(22) PCT Filed: Feb. 27, 2013

(86) PCT No.: PCT/JP2013/055129
§ 371 (c)(1),
(2) Date: Oct. 20, 2014

(87) PCT Pub. No.: WO2013/161377
PCT Pub. Date: Oct. 31, 2013

(65) Prior Publication Data
US 2015/0112081 A1 Apr. 23, 2015

(30) Foreign Application Priority Data
Apr. 26, 2012 (JP) ................. 2012-101625

(51) Int. Cl.
*C07D 231/00* (2006.01)
*H01L 51/00* (2006.01)
*C07D 513/04* (2006.01)
*C07F 7/02* (2006.01)

(52) U.S. Cl.
CPC .......... *H01L 51/0071* (2013.01); *C07D 513/04* (2013.01); *C07F 7/025* (2013.01); *H01L 51/008* (2013.01)

(58) Field of Classification Search
CPC ...... C07F 5/025; C07F 7/0812; C07F 7/0854; C07F 7/1836; C07F 7/1856; C07D 271/12; C07D 285/14; C07D 513/04; C07D 498/04; C07D 513/18
USPC ................................. 548/110, 126
See application file for complete search history.

(56) References Cited

FOREIGN PATENT DOCUMENTS

| CN | 102060282 A | 5/2011 | |
|---|---|---|---|
| CN | 102083883 | 6/2011 | |
| EP | 2266982 A1 * | 12/2010 | ............ C07D 17/14 |
| JP | 2002-505663 A | 2/2002 | |
| JP | 2011-119435 | 6/2011 | |
| JP | 2011-528383 | 11/2011 | |
| JP | 2011-247992 | 12/2011 | |

OTHER PUBLICATIONS

Wang, M., X. Hu, P. Liu, W. Li, X. Gong, F. Huang, and Y. Cao "Donor-Acceptor Conjugated Polymer based on Naphtho[1,2-c:5,6-c]bis[1,2,5] thiadiazole for High-Performance Polymer Solar Cells" Journal of the American Chemical Society (2011), 133 (25), pp. 9638-9641.*
Osaka, I., M. Shimawaki, H. Mori, I. Doi, E. Miyazaki, T. Koganezawa, and K. Takimiya "Synthesis, Characterization, and Transistor and Solar Cell Applications of a Napthobisthiadiazole-Based Semiconducting Polymer" Journal of the American Chemical Society (2012), 134 (7), pp. 3498-3507.*
Darses, Sylvain et al., "Potassium Organotrifluoroborates: New Perspectives in Organic Synthesis", Chem. Rev. vol. 108, pp. 288-325, 2008.
Mataka, Shuntaro et al., "Sulfur Nitride in Organic Chemistry. Part 19. 1) Selective Formation of Benzo- and Benzobis[1,2,5]thiadiazole Skeleton in the Reaction of Tetrasulfur Tetranidrite with Naphthalenols and Related Compounds", The Chemical Society of Japan, vol. 64, No. 1, pp. 68-73, 1991.
Osaka, Itaru et al., "Synthesis, Characterization, and Transistor and Solar Cell Applications of a Naphthobisthiadiazole-Based Semiconducting Polymer", Journal of the American Chemical Society, vol. 134, pp. 3498-3507, 2012.
Wang, Ming et al., Donor-Acceptor Conjugated Polymer Based on Naphtho[1,2-c:5,6-c]bis[1,2,5]thiadiazole for High-Performance Polymer Solar Cells, Journal of the American Chemical Society, vol. 133, pp. 9638-9641, 2011.
Yamamoto, Yasunori et al., "Cyclic Triolborates: Air-and Water-Stable Ate Complexes of Organoboronic Acids", Angew. Chem. Int, Ed. vol. 47, pp. 928-931, 2008.
CN2013380021148.7, Chinese Office Action, Issued Jul. 27, 2015.
Bogyu Lim et al., Synthesis of an alternating thienylenevinylene-benzothiadiazole copolymer with high hole mobility for use in organic solar cells. Organic Electronics, 2010, 11(11) pp. 1772-1778.
EP13782014.8, Extended European Search Report, Apr. 8, 2015.

* cited by examiner

Primary Examiner — Nyeemah A Grazier
Assistant Examiner — Sagar Patel
(74) Attorney, Agent, or Firm — K&L Gates, LLP; Louis Cullman; Michelle Glasky Bergman

(57) ABSTRACT

A naphthobisthiadiazole derivative is represented by Formula 1. In Formula 1, Z is selected from a hydrogen atom, a boronic acid group, a boronic acid ester group, a trifluoroborate salt group and a triolborate salt group, and at least one Z is a boronic acid group, a boronic acid ester group, a trifluoroborate salt group or a triolborate salt group. The naphthobisthiadiazole derivative is an organoboron compound, and can be converted to various compounds by a Suzuki-Miyaura coupling reaction; thus, is applicable as a precursor of complex compounds. Using the naphthobisthiadiazole derivative, research, development, and practical applications of low molecular weight compounds and high-molecular compounds useful for various organic semiconductor materials and the like can be ensured.

(1)

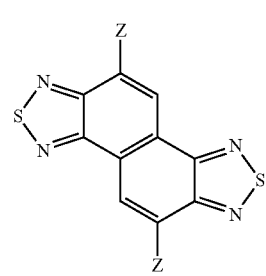

2 Claims, No Drawings

NAPHTHOBISTHIADIAZOLE DERIVATIVE

TECHNICAL FIELD

The present disclosure relates to naphthobisthiadiazole derivatives.

BACKGROUND ART

Research, development, and practical applications of various organic semiconductor materials are progressing, and organic semiconductor materials having a naphthobisthiadiazole skeleton have a key role. Non-Patent Literature 1 discloses a high-molecular compound having a naphthobisthiadiazole skeleton and the synthesis process thereof.

CITATION LIST

Non-Patent Literature

[Non-Patent Literature 1]
Ming Wang, Xiaowen Hu, Peng Liu, Wei Li, Xiong Gong, Fei Huang, and Yong Cao; "Donor-Acceptor Conjugated Polymer Based on Naphtho[1,2-c:5,6-c]bis[1,2,5]thiadiazole for High Performance Polymer Solar cells"; *J. Am. Chem. Soc.*, 133, 9638-9641 (2011).

SUMMARY OF INVENTION

Technical Problem

In Non-Patent Literature 1, naphthobisthiadiazole is brominated and this bromine compound and an aromatic ring or a heteroaromatic ring such as a thiophene ring including an organic metal, for example, organotin were combined using a transition metal catalyst to obtain a high-molecular compound that can be used as an organic semiconductor material. This approach, however, has issues that this approach lacks versatility as organic metals cannot be introduced to some heteroaromatic rings or aromatic rings that are to be bound and/or substances, such as, organotin are toxic, which makes its industrial applicability difficult.

The present disclosure is made in view of the aforementioned problems, and the objective of the present disclosure is to provide naphthobisthiadiazole derivatives that can be expanded into various organic semiconductor materials having a naphthobisthiadiazole skeleton, and is suited for many general-purpose applications.

Solution to Problem

A naphthobisthiadiazole derivative according to the present disclosure is represented by Formula 1,

[Chemical Formula 1]

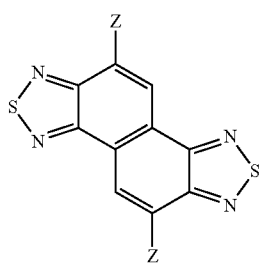

(1)

where Z is selected from a hydrogen atom, a boronic acid group, a boronic acid ester group, a trifluoroborate salt group and a triolborate salt group, and at least one Z is a boronic acid group, a boronic acid ester group, a trifluoroborate salt group or a triolborate salt group.

Z is preferably represented by any one of Formula 11 to Formula 19,

[Chemical Formula 2]

 (11)

 (12)

 (13)

 (14)

 (15)

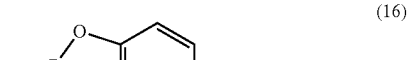 (16)

 (17)

 (18)

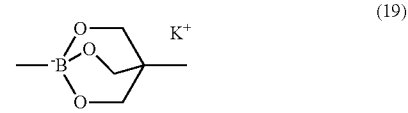 (19)

where, in Formula 12, R is selected from an alkyl group.

Advantageous Effects of Invention

A naphthobisthiadiazole derivative according to the present disclosure includes a boronic acid group, a boronic acid ester group, a trifluoroborate salt group or a triolborate salt group. The boronic acid group, the boronic acid ester group, the trifluoroborate salt group and the triolborate salt group can be converted to various compounds using coupling reactions such as a Suzuki-Miyaura coupling reaction; thus, are suited for many general-purpose applications as a precursor of complex compounds. Using the naphthobisthiadiazole derivative, research, development, and practical applications of low molecular weight compounds and high-molecular compounds, the low molecular weight compounds and the high-molecular compounds having a useful naphthobisthiadiazole skeleton for various organic semiconductor materials and the like can be ensured.

DESCRIPTION OF EMBODIMENTS

Naphthobisthiadiazole Derivative

A naphthobisthiadiazole derivative according to the present embodiment is represented by Formula 1.

[Chemical Formula 3]

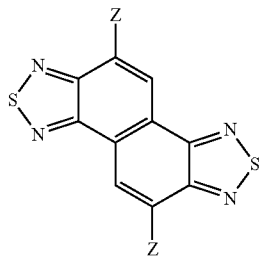

(1)

In Formula 1 above, Z is selected from a hydrogen, a boronic acid group, a boronic acid ester group, a trifluoroborate salt group and a triolborate salt group, and at least one Z is a boronic acid group, a boronic acid ester group, a trifluoroborate salt group or a triolborate salt group. The boronic acid group, the boronic acid ester group, the trifluoroborate salt group and the triolborate salt group are not particularly limited, but may include functional groups represented by Formula 11 to Formula 19. In Formula 12, R is selected from an alkyl group.

[Chemical Formula 4]

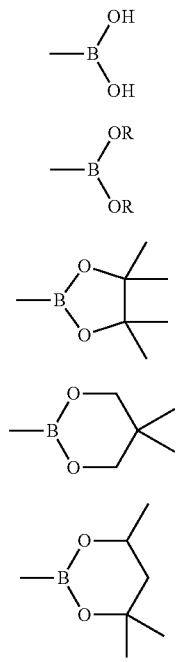

(11)
(12)
(13)
(14)
(15)
(16)
(17)
(18)
(19)

-continued

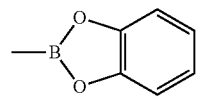

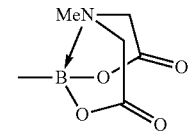

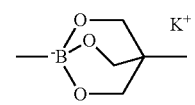

A naphthobisthiadiazole derivative is an organoboron compound, and can be converted to various compounds using coupling reactions such as a Suzuki-Miyaura coupling reaction; thus, can be used as a precursor of complex compounds.

Here, a naphthobisthiadiazole derivative and halide, the halide having, for example, a pi-electron conjugated structure, which includes a donor functional group, an acceptor functional group, a thiophene ring, and the like, are reacted. This may achieve a simple synthesis of a low molecular weight compound, a high-molecular compound, and the like, which have a naphthobisthiadiazole skeleton.

Thus, using the naphthobisthiadiazole derivative, research, development, and practical applications of low molecular weight compounds and high-molecular compounds having a useful naphthobisthiadiazole skeleton for various organic semiconductor materials and the like can be ensured. Further, the naphthobisthiadiazole derivative is relatively stable in water, air and the like, and is easy to handle.

(Synthesis Process of Naphthobisthiadiazole Derivative)

A synthesis process of the naphthobisthiadiazole derivative of the aforementioned embodiment is not particularly limited, but a synthesis process can be performed by combining publicly-known synthesis processes. Syntheses may include the following synthesis, for example.

Naphthobisthiadiazole(naphtho[1,2-c:5,6-c']bis[1,2,5] thiadiazole) may be reacted with a diboronic acid ester. Bonds of carbons atoms of the naphthobisthiadiazole with hydrogen atoms are cut, the carbon atoms being at the 4th position and at the 9th position, and a boronic acid ester group is bound to each of the same positions to obtain the naphthobisthiadiazole derivative represented by Formula 1.

[Chemical Formula 5]

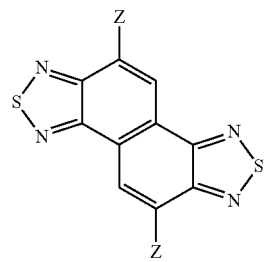

A diboronic acid ester used is not particularly limited, and the diboronic acid esters may include, for example, bis(pinacolato)diboron, bis(neopentyl glycolato)diboron, bis(hexylene glycolato)diboron and bis(catecholato)diboron.

Here, a reaction by adding a C—H bond activation catalyst may be preferable. This allows the bonds of carbons atoms of the naphthobisthiadiazole with hydrogen atoms, the carbon atoms being at the 4th position and at the 9th position, to be easily cut. Consequently, forming of a bond between the carbon atom, from which a hydrogen atom is eliminated, and a boronic acid ester group is accelerated. The C—H bond activation catalyst is not limited as long as the catalyst cuts a carbon-hydrogen bond; thus, may include transition metals, such as, palladium, iridium and ruthenium, or catalysts that contain these transition metals. When iridium or a catalyst containing iridium serves as a C—H bond activation catalyst, a compound that functions as a ligand may be added.

Furthermore, a naphthobisthiadiazole derivative that contains a boronic acid can be obtained by de-esterifying the naphthobisthiadiazole derivative that contains a boronic acid ester.

Yet further, a naphthobisthiadiazole derivative that contains a trifluoroborate salt group or a triolborate salt group can be obtained using a naphthobisthiadiazole derivative that includes a boronic acid or a boronic acid ester through the process disclosed, for example, in Potassium Organotrifluoroborates: New Perspectives in Organic Synthesis; Sylvain Darses and Jean-Pierre Genet, *Chem. Rev.*, 108, 288-325 (2008), and Cyclic Triolborates: Air- and Water-Stable Ate Complexes of Organoboronic Acids; Yasunori Yamamoto, Miho Takizawa, Xiao-Qiang Yu, Norio Miyaura, *Angewandte Chemie International Edition*, 47, 928-931 (2007).

Dibromonaphthothiadiazole(4,9-dibromonaphtho[1,2-c:5,6-c']bis[1,2,5]thiadiazole) may be reacted with a diboronic acid ester to synthesize a naphthobisthiadiazole derivative that contains a boronic acid ester group.

Naphthobisthiadiazole(naphtho[1,2-c:5,6-c']bis[1,2,5]thiadiazole) and dibromonaphthothiadiazole(4,9-dibromonaphtho[1,2-c:5,6-c']bis[1,2,5]thiadiazole) can be obtained through the process disclosed in Sulfur Nitride in Organic Chemistry, Part 19, Selective Formation of Benzo- and Benzobis[1,2,5]thiadiazole Skeleton in the Reaction of Tetrasulfur Tetranitride with Naphthalenols and Related Compounds; Shuntaro Mataka, Kazufumi Takahashi, Youji Ikezaki, Taizo Hatta, Akiyoshi Torii, and Masashi Tashiro; *Bull. Chem. Soc. Jpn.*, 64, 68-73 (1991).

EXAMPLES

Hereinafter, a naphthobisthiadiazole derivative and the synthesis process thereof are discussed in view of examples, but unless otherwise claimed, these examples are not intended to limits the claims.

(Synthesis of naphtho[1,2-c:5,6-c']bis[1,2,5]thiadiazole-4,9-bis(boronic acid pinacol ester) (hereinafter referred to as Compound 1))

Under a nitrogen atmosphere, cyclohexane (20 ml) as a solvent, bis(1,5-cyclooctadiene)di-μ-methoxydiiridium(I) (33 mg, 0.05 mmol) as a C—H bond activation catalyst, and 4,4'-di-tert-butyl-2,2'-dipyridyl compound (27 mg, 0.1 mmol) as a ligand of the C—H bond activation catalyst were added to a three-necked flask, and were stirred at reflux in the dark for about 1 hour.

Next, bis(pinacolato)diboron (283 mg, 1.1 mmol) was added to the resultant, and the mixture was held at reflux for 30 mins.

Thereafter, naphtho[1,2-c:5,6-c']bis[1,2,5]thiadiazole (122 mg, 0.5 mmol) was added to hold at reflux for 12 hours.

The mixture was cooled to room temperature, cyclohexane was removed, and the crude product was recrystallized using chloroform to yield slightly-whitish needle crystals, Compound 1 (174 mg, 70%).

The reaction formula is shown below.

[Chemical Formula 6]

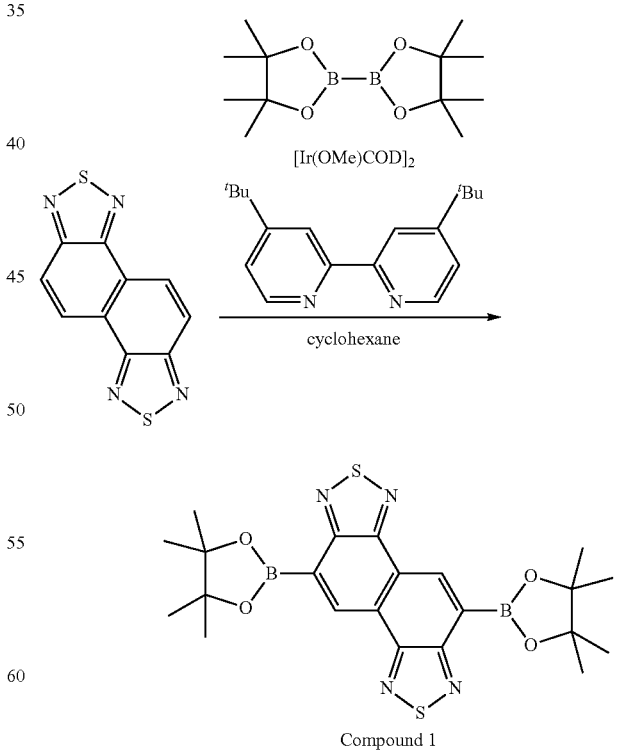

Compound 1

The experimental results of obtained Compound 1 are summarized below. $^1$H-NMR (400 MHz, CDCl$_3$, ppm) δ 1.50 (s, 24H, CH$_3$), 9.52 (s, 2H, ArH)

(Synthesis of 4,9-bis(thiophene-2-yl)-naphtho[1,2-c: 5,6-c']bis[1,2,5]thiadiazole (hereinafter referred to as Compound 2))

Under a nitrogen atmosphere, Compound 1 (99.2 mg, 0.2 mmol), 2-bromothiophene (72.7 mg, 0.44 mmol), Pd(PPh$_3$)$_4$ (4.8 mg, 0.004 mmol), potassium carbonate (1.11 g, 8 mmol), distilled water (4 ml) and toluene (10 ml) were added to a three-necked flask and the mixture was stirred at reflux for 12 hours.

The reaction solution was allowed to cool to room temperature, water was poured thereinto, and a deposited solid was obtained by filtering. Recrystallization of the resulting solid using chloroform yielded a red solid, Compound 2 (67 mg, 82%).

The reaction formula is shown below.

[Chemical Formula 7]

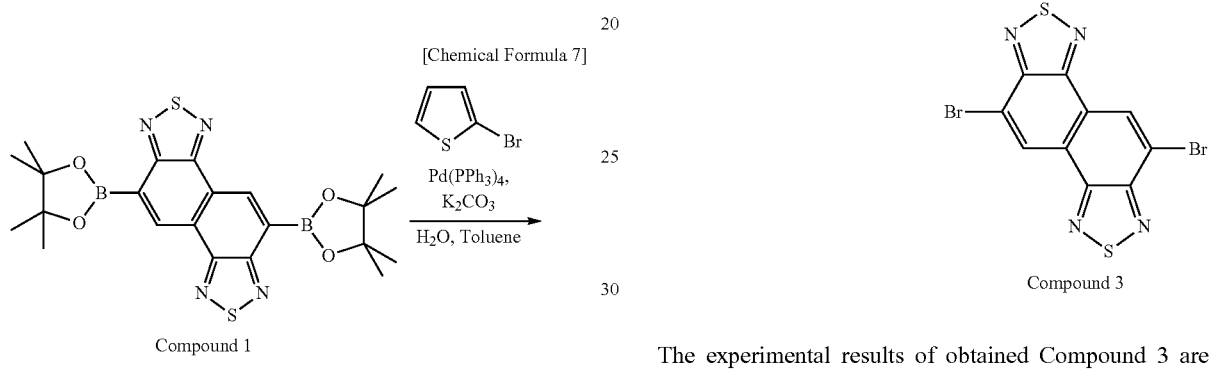

Compound 2

The experimental results of obtained Compound 2 are summarized below. $^1$H-NMR (400 MHz, CDCl$_3$, ppm) δ 7.29 (d, 2H, ArH), 7.55 (d, 2H, ArH), 8.33 (d, 2H, ArH), 8.99 (s, 2H)

(Synthesis of 4,9-dibromonaphtho[1,2-c:5,6-c']bis[1,2,5]thiadiazole (hereinafter referred to as Compound 3))

To a reaction container, Compound 1 (49.6 mg, 0.1 mmol), copper (II) bromide (134 mg, 0.6 mmol), methanol (4 ml), distilled water (2 ml) and NMP (12 ml) were added to reflux. After cooling, the deposited solid was isolated by filtering. Thereafter, the resultant was washed with hydrochloric acid, water and methanol to yield Compound 3 (3 mg, 70%).

The reaction formula is shown below.

[Chemical Formula 8]

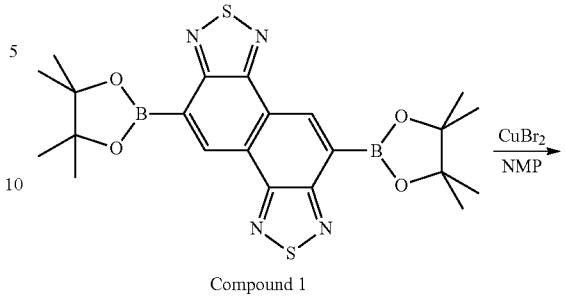

Compound 1

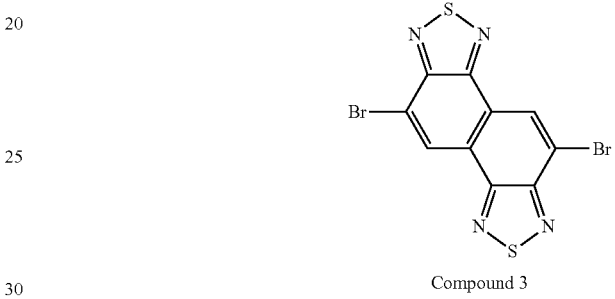

Compound 3

The experimental results of obtained Compound 3 are summarized below. $^1$H-NMR (400 MHz, CDCl$_3$, ppm) δ 9.14 (s, 2H, ArH)

(Synthesis of poly {naphtho[1,2-c:5,6-c']bis[1,2,5]thiadiazole-4,9-diyl-alt-(3'4'''-di(2-decyltetradecyl)-2,2';5',2'';5''',2'''-quarter thiophen-5,5'''-diyl)} (Compound 4))

Under a nitrogen atmosphere, Compound 1 (24.8 mg, 0.05 mmol), Compound A (58.1 mg, 0.05 mmol), Pd(PPh$_3$)$_2$Cl$_2$ (1.7 mg, 0.0025 mmol), 2M K$_2$CO$_3$ solution (1.6 ml), toluene (2.4 ml) and one drop of Aliquat 336 were put into a reaction vial, and the reaction vial was sealed.

The vial was placed in a microwave synthesizer, and was left reacting for 2 hours at 180° C. A large excess of methanol was then poured into the reaction solution, and the solution was stirred.

The precipitate was removed using a Soxhlet extraction filter, and, by Soxhlet extraction using methanol and chloroform, components that are soluble in these solvents were removed.

The residue in the filter was further extracted by Soxhlet extraction using chlorobenzene, and a large excess of methanol was poured into the obtained solution.

The precipitate was filtered to yield a dark-green solid, Compound 4 (27 mg, 43%).

The reaction formula is shown below.

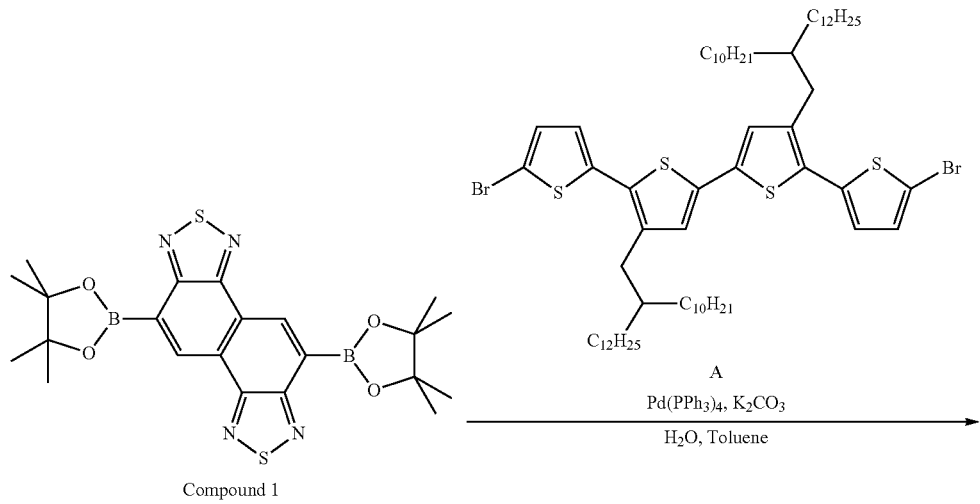

The experimental results of obtained Compound 4 are summarized below. $^1$H-NMR (400 MHz, CDCl$_3$, ppm) about δ 9.0 (br, 2H, ArH), about δ 7 to 8 (br, 6H, ArH), about δ 2.5 (br, 4H), about δ 0.8 to 2 (br, 94H)

The present disclosure can have various embodiments and modifications within the scope of the present disclosure. Moreover, the aforementioned embodiments are for explaining the present disclosure, and are not to limit the scope of the present disclosure.

This application claims the benefit of Japanese Patent Application No. 2012-101625, filed on Apr. 26, 2012. The entire disclosure of the specification and the claims of Japanese Patent Application No. 2012-101625 is incorporated by reference herein.

INDUSTRIAL APPLICABILITY

As discussed above, a naphthobisthiadiazole derivative can be converted to various compounds using coupling reactions such as a Suzuki-Miyaura coupling reaction, can be used as a precursor of complex compounds, and is suited for many general-purpose applications. Using the naphthobisthiadiazole derivative, research, development, and practical applications of low molecular weight compounds and high-molecular compounds having a useful naphthobisthiadiazole skeleton for various organic semiconductor materials and the like can be ensured.

The invention claimed is:

1. A naphthobisthiadiazole compound of Formula 1:

Formula 1

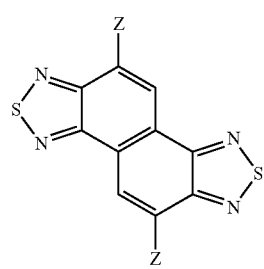

(1)

wherein Z is selected from a hydrogen atom, a boronic acid group, a boronic acid ester group, a trifluoroborate salt group, or a triolborate salt group; and at least one Z is a boronic acid group, a boronic acid ester group, a trifluoroborate salt group, or a triolborate salt group.

2. The naphthobisthiadiazole compound according to claim 1, wherein Z is represented by any one of Formula 11 to Formula 19, Formula 2

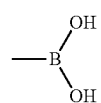

(11)

-continued
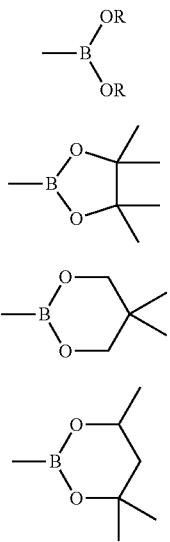
(12)
(13)
(14)
(15)
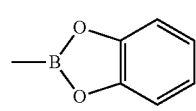
(16)
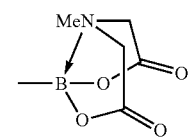
(17)
(18)
—BF$_3^-$ K$^+$
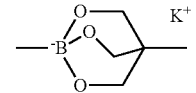
(19)
wherein, in Formula 12, R is selected from an alkyl group.
* * * * *